United States Patent
Rui et al.

(10) Patent No.: US 8,349,584 B2
(45) Date of Patent: Jan. 8, 2013

(54) MICROARRAYS AND THEIR MANUFACTURE

(75) Inventors: Hallgeir Rui, Gladwyne, PA (US); Matthew J. LeBaron, Rhodes, MI (US)

(73) Assignee: Georgetown University, Washington, DC (US)

( * ) Notice: Subject to any disclaimer, the term of this patent is extended or adjusted under 35 U.S.C. 154(b) by 335 days.

(21) Appl. No.: 11/409,717

(22) Filed: Apr. 24, 2006

(65) Prior Publication Data

US 2006/0257908 A1    Nov. 16, 2006

Related U.S. Application Data

(63) Continuation-in-part of application No. PCT/US2004/035209, filed on Oct. 22, 2004.

(60) Provisional application No. 60/513,197, filed on Oct. 23, 2003.

(51) Int. Cl.
*G01N 1/28* (2006.01)

(52) U.S. Cl. .................... 435/40.52; 435/40.5

(58) Field of Classification Search .......... None
See application file for complete search history.

(56) References Cited

U.S. PATENT DOCUMENTS

| | | | |
|---|---|---|---|
| 4,497,792 A | 2/1985 | Gindler | |
| 4,647,543 A | 3/1987 | Stocker et al. | |
| 4,684,609 A | 8/1987 | Hsu | |
| 4,695,339 A | 9/1987 | Rada | |
| 4,752,347 A | 6/1988 | Rada | |
| 4,801,553 A | 1/1989 | Owen et al. | |
| 4,820,504 A * | 4/1989 | Battifora | 435/7.23 |
| 4,914,022 A * | 4/1990 | Furmanski et al. | 435/7.21 |
| 4,946,669 A | 8/1990 | Siegfried et al. | |
| 5,002,377 A | 3/1991 | Battifora et al. | |
| 5,143,714 A | 9/1992 | Cosgrove et al. | |
| 5,156,019 A | 10/1992 | McCormick | |
| 5,244,787 A | 9/1993 | Key et al. | |
| 5,252,487 A | 10/1993 | Bacus et al. | |
| 5,281,521 A | 1/1994 | Trojanowski et al. | |
| 5,290,706 A | 3/1994 | Camiener | |
| 5,411,885 A | 5/1995 | Marx | |
| 5,427,742 A | 6/1995 | Holland | |
| 5,431,952 A | 7/1995 | Ocello | |
| 5,432,056 A | 7/1995 | Hartman et al. | |
| 5,452,584 A | 9/1995 | Diggs | |

(Continued)

FOREIGN PATENT DOCUMENTS

WO    WO-9617246 A1    6/1996

(Continued)

OTHER PUBLICATIONS

Borden, M., M. Attawia, et al. (2002). "The sintered microsphere matrix for bone tissue enginerring: in vitro osteoconductivity studies." *J Biomed Mater Res* 61 (3): 421-9.

(Continued)

*Primary Examiner* — Allison Ford
(74) *Attorney, Agent, or Firm* — Foley Hoag LLP

(57) ABSTRACT

The present invention relates to a method for creating two- and three-dimensional arrays. Plates of sample materials are stacked to create primary stacks. Primary stacks are sliced to form combs. Combs are stacked to form secondary stacks. Secondary stacks are sliced to form tertiary plates or two-dimensional arrays. Tertiary plates can be stacked to form three-dimensional arrays. The two- and three-dimensional arrays can be used in large-scale parallel processing of samples, pattern printing, tissue engineering, microfluidics, microelectronics, and microconstruction.

13 Claims, 3 Drawing Sheets

U.S. PATENT DOCUMENTS

| | | | |
|---|---|---|---|
| 5,487,975 | A | 1/1996 | Miller et al. |
| 5,514,378 | A | 5/1996 | Mikos et al. |
| 5,550,033 | A | 8/1996 | Krumdieck |
| 5,597,692 | A | 1/1997 | Coghlan et al. |
| 5,614,376 | A | 3/1997 | Copley et al. |
| 5,665,398 | A | 9/1997 | McCormick |
| 5,700,656 | A | 12/1997 | Liu |
| 5,750,340 | A | 5/1998 | Kim et al. |
| 5,776,298 | A | 7/1998 | Franks |
| 5,784,162 | A | 7/1998 | Cabib et al. |
| 5,817,032 | A | 10/1998 | Williamson, IV et al. |
| 5,888,733 | A | 3/1999 | Hyldig-Nielsen et al. |
| 5,983,991 | A | 11/1999 | Franks |
| 6,022,700 | A | 2/2000 | Monks et al. |
| 6,103,518 | A | 8/2000 | Leighton |
| 6,140,135 | A * | 10/2000 | Landegren et al. ........... 436/518 |
| 6,199,623 | B1 | 3/2001 | Franks |
| 6,536,219 | B2 | 3/2003 | Peters |
| 6,576,019 | B1 | 6/2003 | Atala |
| 6,615,592 | B2 | 9/2003 | Prien et al. |
| 6,696,271 | B2 | 2/2004 | Slamon et al. |
| 6,699,710 | B1 | 3/2004 | Kononen et al. |
| 6,746,848 | B2 | 6/2004 | Smith |
| 6,780,636 | B2 | 8/2004 | Mastorides et al. |
| 6,900,009 | B2 | 5/2005 | Schiller et al. |
| 6,946,297 | B2 | 9/2005 | Dorn |
| 2002/0094533 | A1 | 7/2002 | Hess et al. |
| 2005/0170501 | A1* | 8/2005 | Auger et al. .................. 435/366 |
| 2006/0046282 | A1 | 3/2006 | Hewitt |

FOREIGN PATENT DOCUMENTS

| | | | |
|---|---|---|---|
| WO | WO-98/52691 | A1 | 11/1998 |
| WO | WO-0210761 | A1 | 2/2002 |
| WO | WO-0242736 | A2 | 5/2002 |
| WO | WO-2005/040348 | | 5/2005 |

OTHER PUBLICATIONS

Bubendorf, L., B. Grilli, et al. (2001a)."Multiprobe FISH for enhanced detection of bladder cancer in voided urine specimens and bladder washings." *Am J Clin Pathol* 116 (1) : 79-86.

Bubendorf, L., J. Kononen, et al. (1999). "Survey of gene amplifications during prostate cancer progression by high-throughout fluorescence in situ hybridization on tissue microarrays." Cancer Res 59 (4): 803-6.

Bubendorf, L., A. Nocito, et al. (2001b). "Tissue microarray (TMA) technology: miniaturized pathology archives for high-throughput in situ studies." *J Pathol* 195 (1) : 72-9.

Bundy, J. L. and C. Fenselau (2001)."Lectin and carbohydrate affinity capture surfaces for mass spectrometric analysis of microorganisms." *Anal Chem* 73 (4): 751-7.

Chin, K. V. and A. N. Kong (2002)."Application of DNA microarrays in pharmacogenomics andtoxicogenomics." *Pharm Res* 19 (12): 1773-8.

Ciapetti, G., L. Ambrosio, et al. (2003) "Osteoblast growth and function in porous poly varepsilon-caprolactone matrices for bone repair: a preliminary study." *Biomaterials* 24 (21): 3815-24.

Gracey, A. Y. and A. R. Cossins (2003). "Application of microarray technology in enviromental and comparative physiology." *Annu Rev Physio* 65 : 231-59.

Harris, T. M., A. Massimi, et al. (2000). "Injecting new ideas into microarray printing." *Nat Biotechnol* 18 (4) : 384-5.

Kononen, J., L. Bubendorf, et al. (1998). "Tissue microarrays for high-throughput molecular profiling of tumor specimens." Nat Med 4 (7): 844-7.

LeBaron, et al., "Ultrahigh Density Microarrays of Solid Samples," Natural Methods, 2(7):511-513 (2005).

Lu, H. H., S. F. El-Amin, et al. (2003) "Three-dimensional, bioactive, biodegradable, polymer-bioactive glass composite scaffolds with improved mechanical properties support collagen synthesis and mineralization of human osteoblast-like cells in vitro." J. Biomed Mater Res 64A (3): 465-74.

Nicoll, S. B., S. Radin, et al. (1997). "In vitro release kinetics of biologically active transforming growth factor-beta 1 from a novel porous glass carrier." Biomaterials 18 (12): 853-9.

Peppas, N. A. and J. J. Sahlin (1996). "Hydrogels as mucoadhesive and bioadhesive materials: a review." Biomaterials 17 (16): 1553-61.

Pollock, J. D. (2002). "Gene expression profiling: methodological challenges, results, and prospects for addiction research." Chem Phys Lipids 121 (1-2): 241-56.

Radin, S., S. Falaize, et al. (2002). "In vitro bioactivity and degradation behavior of silica xerogels intended as controlled release materials." *Biomaterials* 23 (15): 3113-22.

Rimm, D. L., "Tissue Microarrays Without Cores," Nature Methods, 2(7):492-493 (2005).

Rui, et al., "Creating Tissue Microarrays by Cutting-Edge Matrix Assembly," Expert Rev. Med. Devices, 2(6):673-680 (2005).

Ruiz-Taylor, L. A., T. L. Martin, et al. (2001). "Monolayers of derivatized poly(L-lysine)-grafted poly(ethylene glycol) on metal oxides as a class of biomolecular interfaces." *Proc Natl Acad Sci USA* 98 (3): 852-7.

Sahlin, J. J. and N. A. Peppas (1997). "Enhanced hydrogel adhesion by polymer interdiffusin: use of linear poly (ethylene glycol) as an adhesion promoter." J Biomater Sci Polym Ed 8 (6): 421-36.

Schraml, P., J. Kononen, et al. (1999). "Tissue microarrays for gene amplification surveys in many different tumor types." Clin Cancer Res 5 (8): 1966-75.

Tang, Y., E. C. Tehan, et al. (2003). "Sol-gel-derived sensor materials that yield linear calibration plots, high sensitivity, and long-term stability." Anal Cherra 75 (10): 2407-13.

Templin, M. F., D. Stoll, et al. (2002). "Protein microarray technology." Trends Biotechnol 20 (4): 160-6.

Watson, A., A. Mazumder, et al. (1998). "Technology for microarray analysis of gene expression." Curr Opin Biotechnol 9 (6): 609-14.

International Search Report from PCT/US04/35209 dated May 2, 2005.

Supplemental European Search Report for EP 04 79 6242 dated Jul. 12, 2011.

Office Action for CA Application No. 2,543,782 dated Nov. 10, 2011.

* cited by examiner

MICROARRAYS AND THEIR MANUFACTURE

RELATED APPLICATIONS

This application is a continuation-in-part application of PCT/US2004/035209, filed Oct. 22, 2004, which claims priority to U.S. Ser. No. 60/513,197, filed Oct. 23, 2003, the contents of both of which are herein incorporated by reference in their entirety.

FIELD OF THE INVENTION

The present invention relates to a method for constructing two-dimensional (2D) and three-dimensional (3D) patterns and structures. The present invention more particularly relates to preparation of materials for large scale parallel analysis of solid or solidified samples, such as tissue samples. The 2D and 3D microassembled structures prepared according to the present invention have application to other broad fields including pattern printing, tissue engineering, microfluidics, microelectronics, and microconstruction.

BACKGROUND OF THE INVENTION

A method for generating high density arrays of microscopic tissue samples on glass slides has been described and widely adopted (Kononen et al., (1998); Bubendorf et al., (1999); Schraml et al., (1999); Bubendorf et al., (2001a); Bubendorf et al., (2001b); U.S. Pat. No. 6,103,518 to Leighton et al.). However, current methodology to display high density arrays of tissue samples on glass slides for analysis (e.g., microscopy, histochemistry, immunohistochemistry, fluorescent in situ hybridization, etc.) is limited to densities of less than 100 features/cm$^2$. Valuable space is wasted on the array by the residual space between circular features. The current requirement of space in the array is dictated by the cylindrical cores generated by current technology of drilling cores in the tissue or in the medium (e.g., plastic, paraffin, etc.).

Multiple tissues placed on a single pathology slide have been reported by Battifora et al. (U.S. Pat. No. 4,820,504). Using the so-called "sausage technique," numerous tissue chunks were wrapped together in a sheath in an identifiable but disorganized manner for immunohistochemical studies. The arrays of Battifora contained only on the order of a 100 or so tissue features per slide.

Kononen and colleagues have described parallel display of up to 1,000 small tissue or tumor samples of 0.6 mm in diameter on a single microscope slide (about 2 cm×5 cm available surface) that can be processed simultaneously for direct microscopy or scanning or microscopy or scanning afterimmunohistochemical staining or other staining procedures (e.g., regular tissue staining with hematoxylin+eosin, fluorescence-based in situ mRNA or DNA analysis, etc.). The method of Kononen et al. combines innovative placement of tissue cores of up to 10 mm in height into predrilled holes in a paraffin block to assemble a high density of sample cores lined up in parallel. Once a complete collection of tissue cores has been placed in the same tissue block, transverse sections are cut by a microtome, and the resulting 3-10 μm thick sections are transferred to glass slides and adhered or cross-linked to the coated glass. The resulting microarray of small tissue samples can be duplicated many times by cutting multiple sections.

However, the method of Kononen et al. suffers from a number of limitations. Sample density is limited due to needed space between samples to maintain the integrity of the paraffin holding block. Currently, the maximal limit is 1,000 samples per slide (~100 tissue features/cm$^2$). The height of the tissue block is limited due to limitations in the height of each core (0.5 to 1 cm). This height restriction limits the number of theoretical sections to approximately 13,000 sections when cut at 3 μm thickness. This method also promotes inefficient use of samples. Because the method is based on drilling cores out of the primary sample, e.g., a tumor specimen, there will be wasted sample material left between the drilling holes. Core drilling results in reduced quality of the remaining tissue sample, because the integrity of the original sample is broken by the core(s) that are removed (i.e., a "Swiss cheese" effect is produced).

The method of Kononen et al. requires a certain structural rigidity of the sample to work. Softer tissues or materials will be crushed when attempting to remove the core from the drill. Moreover, the method can be most readily used with paraffin-embedded tissue and less readily on frozen tissue or softer gelatinous tissues or material. Finally, although a core-drilling, semi-automated tissue arraying machine has recently been introduced (ATA-27 Automated Arrayer, Beecher Instruments), the core-based semi-automated technology is limited to handling only a low number of specimens at a time, currently a maximum of twenty-six specimens due to the labor-intensive transfer of individual samples to the block. This method is also not readily fully automated due to the manual drilling of cores and placement of individual cores one by one into the predrilled holes. This problem is in part due to the need for movement of the tissue core from sample to block at a central site, with the very limited possibility of gathering and storing cores (samples) before assembly.

The present invention overcomes many of these problems and increases the density of array elements that can be achieved. While the present method is described in detail for tissue arrays, the method has widespread applications as discussed below.

SUMMARY

The present invention provides for a method of microassembling 2D and 3D arrays comprising
  stacking and optionally bonding two or more plates of one or more sample materials to form a primary stack;
  forming a comb by slicing the primary stack perpendicularly to the plane of the two or more plates;
  stacking and optionally bonding two or more combs to form a secondary stack; and
  slicing the secondary stack to form a 2D array.
A 3D array is formed by stacking and optionally bonding two or more 2D arrays.

DETAILED DESCRIPTION OF THE PREFERRED EMBODIMENTS

Figure 1A:
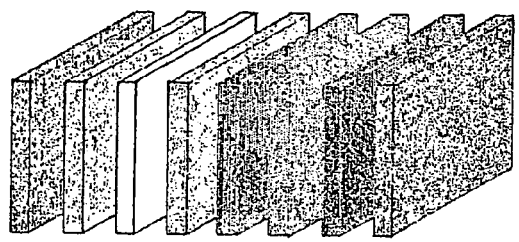
FIGS. 1A-1E are a diagrammatic representation of the steps of the method for creating 2D and 3D arrays.

In general, terms in the present application are used consistent with the manner in which those terms are understood in the art. To aid in the understanding of the specification and claims, the following definitions are provided.

"Primary plate" or "plate" refers to a substantially flat portion or "slice" of material. The primary plate can comprise any number of materials, including tissue (e.g., plant and animal), plastic, polymers, metal, semi-conducting materials, glass, silica-based materials, semi-solid materials such as gels, solidified (e.g., frozen) solutions, suspensions, or colloids, etc., and combinations thereof. The selection of the plate material is usually determined by the purpose of the array to be made therefrom. The primary plates may be generated by several alternative means, including slicing from a larger block, by deposition of material of interest onto a thin support substrate (e.g., plastic, mesh, paper), by embedding of material into thin polymer or gel sheets or slabs, or by derivation directly from sheet-like materials (e.g., plant leaves). The thickness of a primary plate may be determined by the availability or scarcity of the plate material, and/or the intended purpose of the array. Thinner primary plate slices will produce smaller array features and increase the number of array features that will fit in a given area. The size (i.e., the area of the primary plate) is not intended to be limited in any way by the present invention.

"Primary stack" refers to a stack of two or more plates. When complex arrays are constructed with many array elements, the plates are preferably assembled into the primary stack in a predetermined order.

"Comb" refers to a secondary plate generated by taking a "slice" of a primary stack. The secondary plate comprises lengths of usually rectangular portions of each of the plates of the primary stack. Again, the thickness of the slice may be determined, inter alia, by the availability of materials and intended purpose of the array.

"Secondary stack" refers to a stack of two or more combs.

"Tertiary plate" or 2D array refers to a cross-sectioned portion of a secondary stack (i.e., a "slice" taken perpendicularly to the length of the secondary stack) containing several or many array elements. Tertiary plates can be stacked to form a 3D microstructure or array. The thickness of the tertiary plate may be selected based on, inter alia, material availability and/or the intended purpose, e.g., whether the tertiary plate is further stacked to form a 3D array.

Plates and stacks may be "sliced" using any tools known in the art. Freehand slicing can be performed using a razor blade or knife, or other tools (including automated tools) such as a microtome can be utilized for enhanced precision. Because surface shaving of tissue may be used in the methods provided herein, the sample-providing tissue block is left intact without any reduction in quality that is commonly associated with core drilling.

In one embodiment, ultra-high density tissue arrays of thousands of tissue samples may be prepared using the methods provided herein. Currently available methodology to display high density arrays of tissue samples on glass slides is limited to densities of less than 100 features/cm$^2$. Embodiments of the present invention utilize a new methodology that does not rely on drilling of cores and that uses a more practical and space-utilizing method. Limitations of the core-based technology include limited and inconsistent depth of cores, unpredictable content and quality of the tissue cores beneath the surface of the tissue block, limited sample numbers per slide, restricted feature sizes and an inability to array thin-walled, stratified structures such as gut, vessels, or skin. Embodiments of the present invention overcome such limitations, and therefore provide significant advantages over current methodology.

Embodiments of the present invention are not limited to high-density display of tissue samples on a substrate/surface, but can be adapted to high-density, organized 2D display of a variety of samples or reagents (biological, synthetic, inorganic), such as plastics, plants, antibodies, metals, etc. For display of solutes or liquids, these reagents may be made into a solid or semi-solid for section cutting (e.g., by incorporation into a gel or polymer). Embodiments of the present invention can be used to generate high-density arrays of biomolecules such as nucleotides, oligo- and polynucleotides, nucleic acids, amino acids, oligo- and polypeptides, plasmids, proteins, antibodies (Chin and Kong, (2002); Pollock (2002); Templin et al., (2002); Gracey and Cossins, (2003)), which are currently generally printed onto substrates using printing technologies such as pin-based spotting or ink-jet technology (Watson et al., (1998); Harris et al., (2000)). Additionally, arrays of microorganisms such as bacteria and viruses can be created using embodiments of the present invention. In practice, display of macromolecules or microbes can be achieved by embedding the macromolecules or microbes in a gel or polymer so that a semi-solid or solid medium useful for slicing is formed that contains the composition of interest. Macromolecules may also be chemically bonded or conjugated to the polymer or gel matrix to hinder loss, or bleeding, during subsequent manipulation. Chemical binding can include crosslinking that achieves covalent attachment using a series of established chemistries known to those skilled in the art (See, e.g., Hermanson, (1996)), such as glutaraldehyde, formaldehyde, or N-hydroxysuccinimide esters. Chemical binding also includes non-covalent bonding, e.g., via biotin-streptavidin interaction (Bundy and Fenselau, (2001); Ruiz-Taylor et al., (2001)).

When tissue is used to prepare 2D or 3D arrays, a variety of materials can be utilized. The tissues can be paraffin-embedded, quick-frozen, or freeze-dried. Other embedding matrixes known in the art, such as epoxies, waxes, gelatin, agar, polyethylene glycols, polyvinyl alcohols, celloidin, nitrocellulose, methyl and butyl methacrylate resins, polymers, and the like, and combinations thereof, can be used as well as long as the tissue maintains a solid or semi-solid form in order to prepare the plates and stacks of the present method. Paraffin-embedded tissue may be used in a preferred embodiment.

While physical separators may be used in some embodiments of the present invention, these are not necessary for all applications. Even when semi-solid materials are used, other means of segregation can be utilized. For instance, self-healing gels, with thixotropic properties, which spontaneously repair or reestablish themselves after cutting or shearing (e.g., gels made from iota-carrageenans (Bavarian et al., (1996); Parker and Tilly, (1994)), adhesive polymers (e.g., polyethylene glycol), or hydrogels (Peppas and Sahlin, (1996); Sahlin and Peppas, (1997); Tang et al. (2003)), may be used for self-adhesion of gel plates containing different macromolecules without the need for additional bonding agent. For instance, one may place an electrical conducting gel next to a non-conducting gel to generate 2D or 3D electrical circuitry. Alternatively, plates of water-containing gels or substances may be bonded by freezing, also without a specific physical separator. Even when solid materials are used, one may choose to use physical separators as discussed below to identify sample elements in the array.

Furthermore, self-healing or self-adhesive gels containing one or more types of live cells may be used to construct 2D or 3D scaffolds to establish organ-like structures. Alternatively, gels containing immobilized (e.g., chemically cross-linked) antibodies or other binding molecules (e.g., integrins, adhesion molecules) that bind or attract specific cell types may be used. After building a 2D or 3D structure from gel plates according to an embodiment of the invention, the gel can be dried (e.g., by lyophilization) to form a porous scaffold. Gels dried by lyophilization or other means are commonly referred to as xerogels (Nicoll et al., (1997); Radin et al., (2002)). This porous scaffold, which contains a predetermined cellular attraction or binding pattern that will specify binding of cells in 2D or 3D, can be rehydrated and exposed to live cells, which will then form a structure as determined by the materials contained in the scaffold. The gel can comprise biodegradable material (e.g., collagen) and can be sterilized by radiation or chemical means before the addition of live cells to ensure microbe-free growth. This approach can be used to generate functional organs and organ elements (e.g., hair follicles, hormone producing units, kidney elements).

The basic methodology for 2D pattern construction used above can be adapted to 3D pattern construction or microconstruction by organized stacking of sheets of 2D patterns. The ability to systematically build 3D microstructures can be useful for a variety of fields. Micromechanical devices can be assembled by the present methods. Building 2D or 3D networks of variable thickness using materials that are electrically conductive, semiconductive, or insulating or resisting may be useful for microelectronic devices. 2D electrical circuits can be made using a printing technique.

Specifying 3D patterns and microstructures of specific affinity for different cell types in a porous substrate may be useful for advanced 3D tissue engineering and 3D microarrangement of live cells. Building a 3D structure of microchannels is useful for the emerging field of microfluidics. Channels could be generated in the 3D structure by melting, dissolving, or enzymatically digesting elements of differential properties to create a microfluidic device or a tissue lattice. Thus, the present invention provides for a method of preparing a lattice comprising:

creating a 2D or 3D array by
  stacking and optionally bonding two or more plates of one or more sample materials to form a primary stack;
  forming a comb by slicing the primary stack perpendicularly to the plane of the two or more plates;
  stacking and optionally bonding two or more combs to form a secondary stack;
  slicing the secondary stack to form a 2D array;
  optionally stacking and optionally bonding two or more 2D arrays to form a 3D array; and
  melting, dissolving, or enzymatically digesting some elements of the array to create a lattice.

Another embodiment of the present invention provides for a method of preparing a microfluidic device comprising:

creating a 2D or 3D array by
  stacking and optionally bonding two or more plates of one or more sample materials to form a primary stack;
  forming a comb by slicing the primary stack perpendicularly to the plane of the two or more plates;
  stacking and optionally bonding two or more combs to form a secondary stack;
  slicing the secondary stack to form a 2D array;
  optionally stacking and optionally bonding two or more 2D arrays to form a 3D array; and
  melting, dissolving, or enzymatically digesting some elements of the array to create gaps or channels in the 2D or 3D array to prepare a microfluidic device.

High-density arraying of different soluble samples/reagents, including oligonucleotides, plasmids, proteins, etc. onto a solid surface (e.g., glass) is typically achieved by ink-jet technology, or pattern or pin-spot printing. The present method is expected to be useful for depositing these types of 2D arrays without the use of traditional printing equipment. Instead, soluble reagents are made solid or semisolid by freezing, gelling, or otherwise absorbed and embedded onto a substrate from which slices are cut, stacked, and processed as described for the general approach and transferred to the solid surface by sectioning. A distinct benefit of the present methodology is that sample arrays can be stored as blocks and arrays can be cut and "printed" at any time when needed. Certain biological reagents are not stable in liquid form, but are much more stable when dried (e.g., lyophilized), fixed, frozen, or precipitated.

Embodiments of the present invention can approach a maximum of about 10,000 tissue features of a size of about $0.1\ mm^2$ on about 2 cm×about 5 cm area glass slide (or ~1,000 tissue features/$cm^2$), has no immediate height limitation of individual samples (about 100 cm could be possible, corresponding to about 200,000 approximately 5 µm thick sections), effectively uses the primary sample (theoretically, no waste), does not reduce the quality of the leftover primary sample (if not fully used), and works on rigid as well as softer, gelatinous, and frozen tissue. Because embodiments of the present invention do not rely on drilling of cores, but simple generation of slices, individual samples can be precut, and semiautomated or automated assembly can take place by use of a device. Thus, embodiments of the present invention are less labor-intensive and requires less skill than currently available methodology in the art. Finally, embodiments of the present invention are not limited to 2D array building on a substrate, but will allow building/printing of 2D micropatterns that could be useful for broad fields, including microfabrication, microfluidics, electronics, and tissue engineering.

Thus, in one aspect, an array prepared by a method provided herein may comprise at least 1,000 tissue features per slide. In another embodiment, an array prepared by a method provided herein may comprise at least a number of tissue features per slide selected from the group consisting of 2,000; 3,000; 4,000; 5,000; 6,000; 7,000; 8,000; 9,000, and 10,000.

As many as 10,000 parameters, such as macromolecules, may thus be investigated from the same set of tissues, opening new possibilites in array-based screening. Consequently, from an array of 10,000 sample features, serial sectioning and analysis for up to 10,000 different parameters will yield a systematic compilation of $10^8$ tissue image data points.

The general procedure to produce 2D arrays involves stacking primary plates (sections) of sample materials into primary stacks, with subsequent generation of secondary sections (combs) by perpendicular cross-sectional sectioning of primary stacks, followed by bonding of combs into secondary stacks. For 2D arrays/patterns, tertiary sections are generated by cross-sectioning perpendicular to the teeth of the secondary stack of combs, and sections may then be transferred to a support substrate, e.g., glass slide. This procedure, and exemplary arrays resulting therefrom, is demonstrated in FIGS. 1-3.

Plates, stacks, combs, and arrays may be bonded together, and a particular choice of bonding material may depend on the sample material. The bonding material can be, for instance, glue (e.g., acrylate such as cyanoacrylate), paraffin, 2-sided adhesive, epoxies, waxes, polymers such as methyl and butyl acrylate resins and polyvinyl alcohol, gelatin, polyethylene glycol, and the like, and combinations thereof. The plates, stacks, combs, or arrays may be bonded by welding and/or melting. For instance, heat may be used to fuse adjacent plates of paraffin-embedded tissues or cells. However, one skilled in the art will recognize that it is not essential that the plates or stacks are physically bonded together. For instance, it is possible to use embedding in a firm medium (e.g., wax, polymer, etc.) or to use a frame that fits around the plates or stacks and serves to hold them together. The final array can also be held intact by bonding the array to a substrate such as a glass slide.

Direct and lateral bonding of neighboring tissue elements to each other may result in array sections that behave as continuous sheets of fused sample material. Consequently, there is less chance of loss of individual features during sectioning and placement on slides, contrary to core-based arrays where array samples are held together by paraffin.

One of the benefits of the present invention is that sample density can be increased over other known methods. However, it is also possible to add space between samples plates, e.g., a paraffin blank.

Another embodiment of the invention is that by interlacing color-coded or structurally coded "leaves" between the plates in the stacks, microarrays can be generated with built-in orientation so that every feature is framed by a position-unique combination of color/structure. For instance, the plates and stacks can be subdivided into quadrants to delineate samples. One can insert a unique combination of leaves around a particular sample element. This in turn can be used for automated readers to assign values correctly to individual samples, or for the manual analyst to record observations correctly for each of the individual samples. The leaves or physical barriers between array elements, can comprise a wide variety of materials including adhesive, plastics, metal, etc.

By using a variety of labeled bonding materials or physical barriers between array elements, one can enhance the invention by providing unique identifiers around each feature. This is especially useful in a 2D array so that one can identify a sample in the microscope or a microphotograph based on the coding of the four surrounding sides. For simplicity, different colored or patterned two-sided adhesive or glue can be used for each primary plate that is bonded together. Likewise, unique-colored glue may also be used for bonding each of the secondary plates. Varied colored or patterned plastics or other solid dividers may also be added. The dividers may also contain information identifying the sample element in the form of a magnetic strip. As a result, each feature in the final array will be framed by a unique set of four colors that will only occur once in the array provided enough unique colors are used. In addition to color, texture can be modified by adding, e.g., different grainy microparticles or fibers to the bonding material.

The organized display of multiple samples for analysis in a microarray arrangement as described in the Examples below is one use of an embodiment of the invention. The invention can also be presented as a method to specify predetermined patterns or arrangement of samples in two and three dimensions. In the example above with a tissue microarray, a high-density 2D array of tissue squares arranged as quilts or mosaics on a solid support or substrate (e.g., a glass plate).

In one embodiment, a method for preparing arrays involves repeated sectioning and edge-to-edge bonding of samples. Since edge-to-edge bonding permits higher density packing of samples, more replicate samples can fit on a slide for increased redundancy when needed, without compromising individual feature size. Once an array block has been constructed, repeated sectioning such as with a microtome allows for the production of array copies for serial analyses of a large number of parameters or analytes.

The arrays may be based on a self-supported construction that involves sequential bonding and transverse sectioning of stacks of sample plates. Array density may be maximized by rectangular and/or square sample features and, thus, elimination of space loss from a structural scaffold. In contrast, core-based sample arrays require placement of cylindrical sample cores into a structural scaffold such as a paraffin block, typically resulting in arrays where 50% or more of the array area represents scaffold material. Thus, in one embodiment, a prepared array provided herein may be comprised of less than 50% scaffold material. In other embodiments, a prepared array provided herein may be comprised of less than 40%, less than 30%, less than 20%, or less than 10% scaffold material.

While it is preferable that the elements of the array are square or otherwise rectangular (in order to maximize space and minimize waste of material), it is understood that as long as the tissues are maintained in a defined space, various embodiments can be envisioned. It may be desirable to have larger portions of the arrays comprise a particular material.

Larger array features may be preferable for the analysis of certain tissue types, such as heterogenous tissues such as the kidney or gut. Thus, in another embodiment, an array produced by the methods provided herein may have scalable array feature dimensions. The width of each feature equals the thickness of the primary plates, and the length of each feature equals the thickness of the secondary plates. The length and width of each feature may thus be scaled to a desirable size by varying the thickness of the secondary and primary plates, respectively. When a microtome is used for cutting of plates, sample feature dimensions from 5 µm, up to several mm, can be achieved, resulting in continuously tunable widths and lengths of array features. Assembly of small features into high-density microarrays is possible since microscopic sample elements are not handled individually, but instead collectively manipulated many at a time in sizeable continuous sheets. In contrast, core-based punching of tissue blocks is typically restricted to available hollow needles of 0.6, 1, or 2 mm in diameter.

Figure 4:
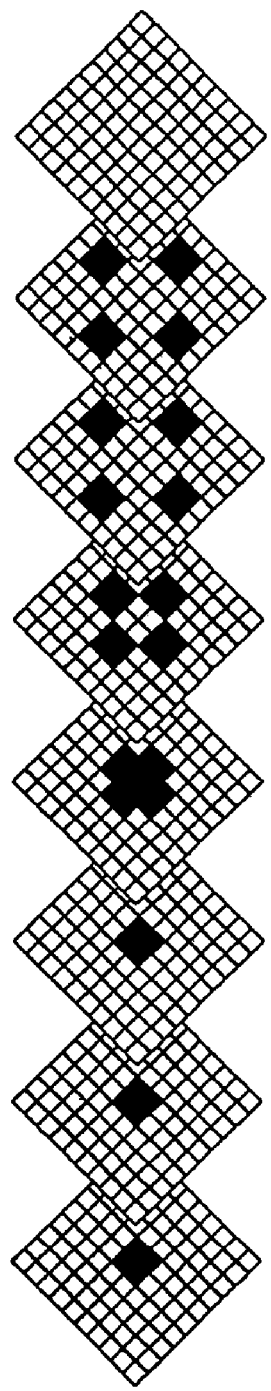
FIG. 4 demonstrates the use of 2D and 3D arrays for creating mosaic patterns for printing or for tissue engineering.

After generating a 2D mosaic pattern, one can extend the array by stacking multiple 2D patterns on top of each other to form 3D patterns. Because the sections can be kept very thin, high resolution, small-scale patterns or microstructures can be achieved. FIG. 4 illustrates generation of a 3D branching structure using the stacking of eight 2D patterns.

Further, the present invention can be used to fashion a 3D scaffold. Scaffold material plates can be alternated with other plates which may be dissolved or melted upon the generation of the secondary stack or tertiary plate. For example, plates of paraffin can be alternated with plates of a higher-melting material. Additional materials may be added into the remaining spaces or cavities. For tissue-engineering applications, e.g., one can seed certain cell types into the spaces. The present technology can be used to print or place antibodies to attract certain types of cells to certain regions of the scaffold.

Once 2D or 3D arrays have been generated, they may be affixed to a substrate or solid support, such as glass or silica plates, plastics, metal, semi-conducting materials, solid porous or non-porous surfaces, polysaccharide-based surfaces, nitrocellulose paper, fabric, and the like, or combinations thereof. For example, the arrays may be adhered to or cross-linked to the solid support.

A novel feature of the methods provided herein is the ability to array thin-walled or sheet-like tissues such as skin, vessels, or gut with polarized or stratified geometry in an oriented manner. For instance, for systemic comparison of drug effects or toxicities on intestinal tissues of animals such as rats, arrays can be generated displaying oriented cross sections of different regions of the gastrointestinal tract from large numbers of animals after treatment for different times, doses, or drug combinations. For example, formalin-fixed gastrointestinal tissue may be trimmed into 10-mm segments of length and used directly as primary plates for bonding into primary stacks. The same approach may be used to generate arrays of other animal or plant tissues that are flat or thin-walled, such as skin, bladder, large vessels, or plant tissues such as leaves. Similarly, arrays of cells may be cultured on support sheets such as polarized cells in a monolayer or cells grown in 3D cultures. The effects of hormones, drugs, or toxins on the cell cultures can be effectively monitored. Since large numbers of treatments or time points can be investigated in parallel, unprecedented spatial and temporal resolution can be achieved.

It is a further object to provide for an array composition prepared by a method provided herein.

EXAMPLES

In addition to the specific materials and methods referred to below, one of skill in the art is directed to the references cited in this application as well as the several Current Protocol guides, which are continuously updated, widely available and published by John Wiley and Sons (New York). In the life sciences, Current Protocols publishes comprehensive manuals in Molecular Biology, Immunology, Human Genetics, Protein Science, Cytometry, Neuroscience, Pharmacology, Cell Biology, Toxicology, and Nucleic Acid Chemistry. Additional sources, including general references for microfluidics, tissue engineering, and microelectronics, are known to one of skill in the art.

Example 1

General Procedure for Constructing a Tissue Microarray

In the case of tissue microarray construction, the procedure involves the following steps (an example of eight different tissues from eight individuals to be represented as a display of a total of 64 sample array is used):

From a block of processed tissue (typically formalin-fixed, paraffinembedded tissue as is routinely used in pathology laboratories), a primary section or plate is cut at the desired thickness. (FIG. 1A). For instance, a plate of the dimension 1 cm by 1 cm at a thickness of 0.1 cm (1 mm). The selected thickness will define the width of the final feature or sample as the sample is represented in the array. The technology allows one to easily vary the size of the final features by using plates of different thickness.

This process is repeated on additional samples to generate a first or primary stack of tissue plates. For instance, a total of 8 samples representing kidney, liver, muscle, heart, stomach, pancreas, spleen, and thyroid gland are processed.

Figure 1B:
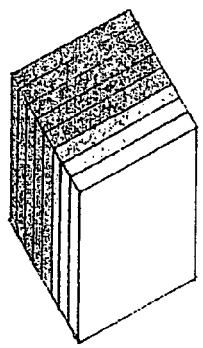

The tissue plates of this primary stack are bonded together so that they form one inseparable unit of plates that are stacked in a predetermined order. (FIG. 1B). The bonding material of preference for tissue stacks is acrylate (e.g., super-glue, or one of the derivative acrylates). In practice, a thin layer of acrylate is added to the top of the first plate, then the second plate is laid on top and weighted down for a few minutes. The process is repeated for each plate. It is possible to save time by adding acrylate to all plates at the same time, and then stacking them and weighting the plates down all at once. This process can also be automated.

Another seven primary stacks are produced from the same tissues from different individuals. The order of the tissues are recorded so that the position of each sample is kept track of. For simplicity, each stack may be composed of the eight tissues arranged in the same order, but that is not a requirement.

Figure 1C:
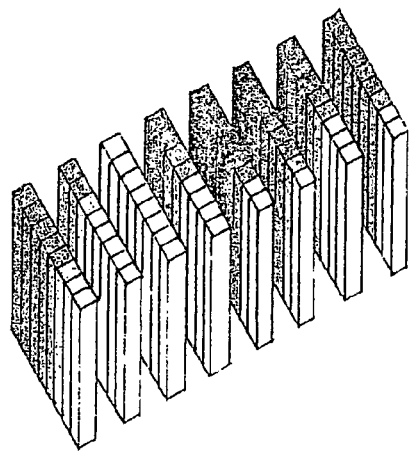

From each bonded stack of tissues, new secondary plates are cut perpendicularly to the plane of the plates. This will result in a secondary plate that resembles a comb, where each tooth of the comb represents each of the eight tissues (FIG. 1C). In the simplest case, the thickness of the cut is maintained at 1 mm (0.1 cm). The thickness of the comb will define the height of the final sample feature as will become apparent. If the thickness of the comb is cut at the same thickness of the primary plates, this will result in square features. However, the method permits variation of the thickness of the comb section, so that rectangular features are possible. This benefit is currently not possible with the existing circular, core-based methodology for tissue array construction, and can be useful for effective display on monitors, film, or print, which typically have aspect ratios different than 1:1 (e.g., 8×10 inch prints can be achieved without image distortion).

Figure 1D:
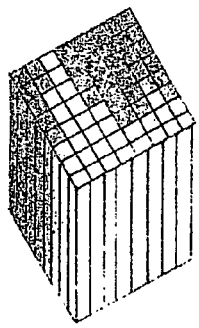

Eight combs (secondary plates) are then stacked and bonded in a predetermined order to form a secondary stack. (FIG. 1D). This secondary stack can be visualized literally as eight hair combs glued together so that the teeth are oriented in the same direction.

The secondary stack is embedded in paraffin so that the teeth of the combs are oriented up, available for sectioning with a histological microtome.

Figure 1E:
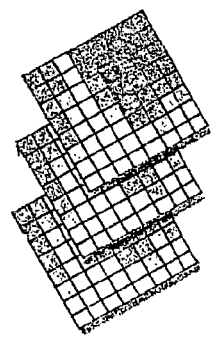

Using the microtome, thin sections are cut in a plane through all the teeth of the combs, resulting in a tertiary plate that contains 8×8 features, each representing one of the 64 original tissue samples. (FIG. 1E). This thin section may be placed on a glass slide using traditional histological techniques, and a microarray of 64 tissue samples is produced. This can then be analyzed by traditional immunohistological staining, immunohistochemistry, in situ hybridization, etc.

Example 2

Generation of a 2D Tissue Array

Figure 2:
FIG. 2 shows an exemplary 2D tissue array generated using the method of the present invention.
Figure 3:
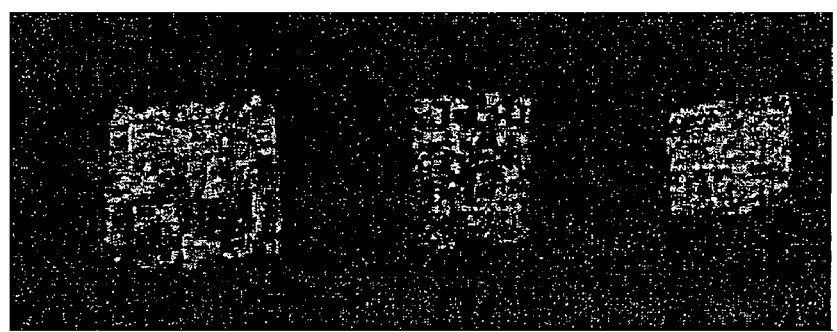
FIG. 3 shows exemplary secondary stacks of tissue arrays for cutting into tertiary plates.

Several paraffin-embedded tissues were sliced by hand to make primary plates of tissue. These tissue plates were bonded together (as a primary stack) with acrylate to keep the individual paraffin-embedded tissue features together. Several primary stacks were sliced by hand across several stacks to create several secondary plates, or combs. Several of the combs were bonded together with acrylate to create a secondary stack. The secondary stack was then sliced using a microtome to create a sample 2D array (or tertiary plate) as shown in FIG. 2 that is 10 μm thick with feature sizes of between 0.25 mm² and 1 mm². The primary and secondary stacks of the tissue array presented in FIG. 2 were prepared freehand (rather than by precise slicing with a microtome), hence the uneven-sized features and the angled section lines. FIG. 3 shows multiple secondary stacks (such as those used to slice the tertiary plate shown in FIG. 2). The various tissue elements used result in a checkerboard appearance of the secondary stacks. The sizes of the cube-shaped secondary stacks in FIG. 3 are approximately 1 cm³ per cube.

Example 3

Applications of 2D and 3D Array for Large-Scale Parallel Analysis

Diagnostic and Screening Arrays

Microarrays are useful for two types of analyses: 1) measuring many analytes (e.g., mRNA, proteins) in one sample, by contacting a sample with a large number of features that represent individual analytes in the microarray, and 2) analyzing many samples displayed in a microarray at once by direct physical, chemical, or image analysis. The present invention is useful for both types of parallel analyses. Solutions of nucleic acids of interest, e.g., oncogenes, etc., may be frozen or incorporated into gels to prepare arrays for diagnostic applications and high-throughput screening. For example, one can construct a 2D array of oligonucleotides of various oncogenes in order to screen individual tumors for particular genotypes or gene expression profiles. Likewise, arrays of protein targets can be used to screen for compounds that bind to a particular target or inhibit/activate an enzyme. Alternatively, arrays could contain both control and neoplastic (or otherwise diseased or abnormal) tissue or sample extract, blood, or liquid that has been immobilized in semi-solid or solid form and displayed in parallel using an embodiment of the present invention. The 2D arrays allow large scale parallel analysis of solid, solidified, or semi-solid samples which is useful, inter alia, in high-throughput screening or large-scale diagnostic clinical applications.

Microfluidics

Microfluidics involves the use of small disposable devices for the handling of biological samples and performing controlled in vitro experiments. For example, microfluidics encompasses the microscopic study of compounds on small numbers of cells. This study is facilitated by the use of microfluidic devices that allow control of the flow of a compound coming into contact with a cell, relying on small volumes to transport both cells and compounds. WO 98/52691 describes sample microfluidic devices. Microfluidic devices can be made using the 2D and 3D arrays created by the present method. To form channels in the microfluidic devices, meltable, dissolvable, or enzymatically digestible material can be used or spaces can be intentionally left in the tertiary plates by using a solid supports that line the sides of a particular array element but that are hollow on the inside. Such an approach may involve removing elements (e.g., by melting or digestion) at the tertiary plate stage, and coating the surface of the tertiary stack (e.g., with glue or cross-linker) before assembly into the 3D tertiary stack. Furthermore, once a 3D block with tunnels is obtained, one can further coat the tunnel surface with, e.g., silicon, thin plastic, or chemical reagents. For example, two types of material can be used as the initial plates to form the primary stack. One material could be a plastic and the other material could be paraffin with a much lower melting point. Once the tertiary plates are stacked to form a 3D array, the array may be subjected to heat to melt the paraffin, leaving the plastic intact. Thus, in such a manner, one can form a 3D array with channels for use in microfluidics. Likewise, microchannels may be useful for the molding of small parts.

Tissue Engineering

The ability to generate 3D microstructures has important applications in biology. Tissue engineering involves fabricating new functional tissue using living cells and a matrix or scaffolding which can be natural, synthetic or combinations of both. One can generate such matrices or scaffolding using 3D arrays prepared according to an embodiment of the present invention. While some progress has been made in generating structurally relatively simple organs such as bone, hairless skin, and bladder, elements or organs with a high degree of microscopic complexity can be generated using an embodiment of the present invention. Tissue engineering of simple trabecular bone typically involves seeding of bone-producing cells, osteoblasts, into a porous, homogenous scaffold without 3D complexity (Borden et al., (2002); Ciapetti et al., (2003); Lu et al., (2003)). U.S. Pat. No. 6,576,019 describes a method for bladder reconstruction. Similarly to the method disclosed in the '019 patent, 2D and 3D matrices of embodiments of the present invention may be used to reconstruct a bladder. Uroepithelial cells can be deposited in one portion of the array and smooth muscle cells can be deposited in a different portion. These matrices can be utilized to provide cells to the desired location in the body in order to accurately guide new tissue development. For instance, using FIG. 4 as an example, the black features could represent gel material containing one cell type, e.g., epithelial cells, while the white features could represent gel material containing another cell type, e.g., supporting fibroblast cells. Complex organs or organ elements can be constructed that contain branching cellular patterns at a micrometer scale, for instance, secretory organs like pancreas or breasts. Biodegradable polymers or substances can be used to construct such arrays. For instance, improved tissue engineering of a) insulin-producing Langerhans islands for patients with Type I diabetes, b) functional kidney elements, or c) skin with hair follicles are just several of numerous possibilities. Hair and skin cells can be made into an array in an alternating pattern.

Pattern Printing

Once secondary stacks or tertiary plates have been created, they can be used to produce pattern prints which can be affixed to a desired surface or fabric. In addition to generating high-density arrays of samples for analysis, one can generate patterns by specifying which individual feature will be localized in a given space (or coordinate) by selecting the correct location of a material in the primary and secondary stack. In other words, one may use this technology to print or specify patterns on a surface, by specifying the location of contrasting elements. A simple checkered pattern can be produced by use of white and black starting material as alternating layers in a primary stack. More advanced patterns could involve multiple colors, or distinct materials that would form 2D patterns of any type. Each feature would represent a square pixel in image terminology. This could be expanded to 3D by overlaying 2D patterns using materials of variable translucency. This could be useful for generation of unique identifiers that can be recognized by appropriate readers.

While the invention has been described and illustrated above by reference to various specific materials, procedures and examples, it is understood that the invention is not restricted to the particular materials, combinations of materials, and procedures selected for that purpose. Numerous variations of such details can be implied and will be appreciated by those skilled in the art.

REFERENCES

Baravian, C., D. Quemada and A. Parker (1996). "Modelling thixotropy using a novel structural kinectics approach: basis and application to a solution of iota carrageenan." *Journal of Texture Studies,* 27, 371-390.

Borden, M., M. Attawia, et al. (2002). "The sintered microsphere matrix for bone tissue enginerring: in vitro osteoconductivity studies." *J Biomed Mater Res* 61 (3): 421-9.

Bubendorf, L., B. Grilli, et al. (2001a). "Multiprobe FISH for enhanced detection of bladder cancer in voided urine specimens and bladder washings." *Am J Clin Pathol* 116 (1): 79-86.

Bubendorf, L., J. Kononen, et al. (1999). "Survey of gene amplifications during prostate cancer progression by high-throughout fluorescence in situ hybridization on tissue microarrays." *Cancer Res* 59 (4): 803-6.

Bubendorf, L., A. Nocito, et al. (2001b). "Tissue microarray (TMA) technology: miniaturized pathology archives for high-throughput in situ studies." *J Pathol* 195 (1): 72-9.

Bundy, J. L. and C. Fenselau (2001). "Lectin and carbohydrate affinity capture surfaces for mass spectrometric analysis of microorganisms." *Anal Chem* 73 (4): 751-7.

Chin, K. V. and A. N. Kong (2002). "Application of DNA microarrays in pharmacogenomics andtoxicogenomics." *Pharm Res* 19 (12): 1773-8.

Ciapetti, G., L. Ambrosio, et al. (2003) "Osteoblast growth and function in porous poly varepsilon-caprolactone matrices for bone repair: a preliminary study." *Biomaterials* 24 (21):3815-24.

Gracey, A. Y. and A. R. Cossins (2003). "Application of microarray technology in enviromental and comparative physiology." *Annu Rev Physio* 65: 231-59.

Harris, T. M., A. Massimi, et al. (2000). "Injecting new ideas into microarray printing." *Nat Biotechnol* 18 (4): 384-5.

Hermanson, G. T. (1996). *Bioconjugate techniques.* San Diego, Academic Press.

Kononen, J., L. Bubendorf, et al. (1998). "Tissue microarrays for high-throughput molecular profiling of tumor specimens." *Nat Med* 4 (7): 844-7.

Lu, H. H., S. F. El-Amin, et al. (2003) "Three-dimensional, bioactive, biodegradable, polymer-bioactive glass composite scaffolds with improved mechanical properties support collagen synthesis and mineralization of human osteoblast-like cells in vitro." *J. Biomed Mater Res* 64A (3): 465-74.

Nicoll, S. B., S. Radin, et al. (1997). "In vitro release kinetics of biologically active transforming growth factor-beta 1 from a novel porous glass carrier." *Biomaterials* 18 (12): 853-9.

Parker, A. and G. Tilly, "Thixotropic carrageenan gels and dairy desserts." In: "Gums and Stabilisers for the Food Industry 7", pp. 393-401. Editors Phillips G. O., Williams, P. A. and Wedlock D. J., Oxford University Press (1994).

Peppas, N. A. and J. J. Sahlin (1996). "Hydrogels as mucoadhesive and bioadhesive materials: a review." *Biomaterials* 17 (16): 1553-61.

Pollock, J. D. (2002). "Gene expression profiling: methodological challenges, results, and prospects for addiction research." *Chem Phys Lipids* 121 (1-2): 241-56.

Radin, S., S. Falaize, et al. (2002). "In vitro bioactivity and degradation behavior of silica xerogels intended as controlled release materials." *Biomaterials* 23 (15): 3113-22.

Ruiz-Taylor, L. A., T. L. Martin, et al. (2001). "Monolayers of derivatized poly(L-lysine)-grafted poly(ethylene glycol) on metal oxides as a class of biomolecular interfaces." *Proc Natl Acad Sci USA* 98 (3): 852-7.

Sahlin, J. J. and N. A. Peppas (1997). "Enhanced hydrogel adhesion by polymer interdiffusin: use of linear poly (ethylene glycol) as an adhesion promoter." *J Biomater Sci Polym Ed* 8 (6): 421-36.

Schraml, P., J. Kononen, et al. (1999). "Tissue microarrays for gene amplification surveys in many different tumor types." *Clin Cancer Res* 5 (8): 1996-75.

What is claimed is:

1. A non-core based array comprising a plurality of square or rectangular shaped tissue samples, each sample being stacked or bonded in a vertical or horizontal direction to a neighboring tissue sample, wherein the tissue samples are systematically arranged in a predetermined order, each sample being identified by a unique code created by material used to bond samples together.

2. The array of claim 1, wherein the dimensions of the tissue samples are in the range of about 5 µm to 0.5 mm.

3. The array of claim 1, wherein the tissue samples comprise paraffin-embedded tissue, frozen tissue, or freeze-dried tissue.

4. The array of claim 1 affixed to a solid support.

5. The array of claim 1, comprising two or more plates or two or more combs bonded to each other.

6. The array of claim 5, wherein the two or more plates or two or more combs are bonded to each other with acrylate, paraffin or other waxes, two-sided adhesive, epoxy, polymers, gelatin, polyethylene glycol, welding, melting or a combination thereof.

7. The array of claim 5, wherein the plates comprise nucleotides, oligonucleotides, polynucleotides, amino acids, oligopeptides, polypeptides, antibodies, plasmids, and/or microorganisms.

8. The array of claim 5, wherein the width and length of the tissue samples are predetermined by cross-sectioning primary and secondary stacks of plates and combs at a desired thickness.

9. The array of claim 1, comprising less than 10% scaffold material.

10. The array of claim 1, comprising at least 1,000 tissue samples.

11. The array of claim 1, comprising at least 10,000 tissue samples.

12. The array of claim 1, comprising about 1,000 tissue samples/cm$^2$.

13. The array of claim 1, which does not have structural scaffold material between tissue samples present on the array.

* * * * *